United States Patent [19]

Errede et al.

[11] Patent Number: 4,722,898

[45] Date of Patent: Feb. 2, 1988

[54] IMMOBILIZATION OF BIOLOGICAL CELLS IN POLYTETRAFLUOROETHYLENE MATRIX

[75] Inventors: Louis A. Errede, North Oaks; George R. Hunt, Mahtomedi, both of Minn.

[73] Assignee: Minnesota Mining and Manufacturing Company, St. Paul, Minn.

[21] Appl. No.: 728,199

[22] Filed: Apr. 29, 1985

[51] Int. Cl.$^4$ .................... C12N 11/04; C12N 11/02; C12N 11/08
[52] U.S. Cl. .................... 435/182; 435/174; 435/177; 435/180
[58] Field of Search ............... 435/174, 176, 177, 180, 435/182

[56] References Cited

U.S. PATENT DOCUMENTS

| | | | |
|---|---|---|---|
| 3,766,013 | 10/1973 | Forgione et al. | 195/63 |
| 3,864,124 | 2/1975 | Breton et al. | 75/212 |
| 4,153,661 | 5/1979 | Ree et al. | 264/120 |
| 4,194,040 | 3/1980 | Breton et al. | 428/308 |
| 4,434,231 | 2/1984 | Jung | 435/253 |
| 4,452,892 | 6/1984 | Rosevear | 435/176 |
| 4,456,685 | 6/1984 | Guthrie | 435/109 |

OTHER PUBLICATIONS

"Basic Biology of New Developments, A. Hollaender, et al., Plenum Press, N.Y. 1983, pp. 465–496.
"The Engineering Mission of NSF Over the Next Decade, Chem. Eng. News, 62, No. 29, Jul. 16, 1984, pp. 22–24.
"Solid Phase Biochemistry" Birnbaum, et al., Scouten, Ed., Wiley, 1983, vol. 66.
Trends in Analytical Chemistry", Kobos, 2, 143 (1983).
Biotechnol, Tso, et al, Lett. 3, 421 (1981).
New Frontiers in Membrane Technology and Chromatography: Applications for Biotechnology" Analytical Chemistry, 56, No. 14, Dec. 1984, pp. 1529–1544A.
"A Renewed Interest in Immobilized Enzymes" Science, 223, 474–476 (1984).

*Primary Examiner*—David M. Naff
*Attorney, Agent, or Firm*—Donald M. Sell; James A. Smith; Lorraine R. Sherman

[57] ABSTRACT

A polytetrafluoroethylene (PTFE) fibril matrix is prepared containing entrapped viable cells such as animal, bacterial, fungal or yeast cells. Cells are blended with surfactant and soap-free PTFE in aqueous dispersion to form a damp paste. Water is added to the paste and a resultant stiff dough is biaxially calendered between calendering rolls to cause fibrillation and form the PTFE fibril matrix. Calendering is preferably carried out at a temperature of 5° to 70° C. and a pressure of 1000 to 3000 MPa. The fibril matrix may be dried.

13 Claims, 6 Drawing Figures

IMMOBILIZATION OF BIOLOGICAL CELLS IN POLYTETRAFLUOROETHYLENE MATRIX

TECHNICAL FIELD

This invention relates to articles which are composite structures and a method therefore, the articles comprising a polytetrafluoroethylene (PTFE) fibril matrix in which is enmeshed and immobilized viable cells. The articles are useful, for example, as industrial catalysts in organic synthesis, fermentation, and removal of chemical pollutants.

BACKGROUND OF THE INVENTION

In the United States high-tech goals are becoming precise. In a recently issued report (see report summary in Chem. Eng. News, 62, no. 29, July 16, 1984, pp. 22-24), entitled "The Engineering Mission of NSF Over the Next Decade," a National Science Board panel suggested as one of fifteen areas of focus for engineering centers of excellence:

"Membrane research for such areas as water desalination, gas separation, metal recovery, water purification, packaging, kidney dialysis, artificial pancreas, and drug release control."

Membrane research has been ongoing since the early 1900's. For example, binding of enzymes to suitable insoluble substrates to render the resultant product commercially useful is known. Such immobilization techniques for microbial cells and enzymes have been classified into three methods: carrier binding method, cross-linking method, and trapping method by I. Chibata in "Basic Biology of New Developments in Biotechnology", A. Hollaender et al., editors, Plenum Press, N.Y., 1983, pp. 465-496. Chibata (supra, at p. 469) has cautioned that these immobilizations should be carried out under very mild conditions to avoid the inactivation of enzymes. It is known that living cells, which contain such enzymes, are even more sensitive than the enzymes, because the conditions that destroy the efficacy of the enzyme will cause the death of the living cell even more easily.

Membrane technology is reviewed by D. C. Warren in "New Frontiers in Membrane Technology and Chromatography: Applications for Biotechnology", Analytical Chemistry, 56, No. 14, December 1984, pages 1529A-1544A.

It is also known in the art to immobilize living cells encased in continuous domains such as alginic acid and polymers. Enzymes adsorbed onto inorganic particulates and then dispersed throughout the interstices of a network of interconnected, interwoven fibers of PTFE (fibrilated PTFE) have been described in U.S. Pat. No. 3,766,013. This patent further teaches that particulate material modified by surface adsorption of enzymes can be mixed with PTFE and the mixture fibrillated into a coherent mass. The ability to fibrilate polytetrafluoroethylene emulsion and mix particulate material with it and then convert the product to a porous sheet has been described in U.S. Pat. No. 4,194,040, and methods for making such fibrillated polymers have been reported in U.S. Pat. Nos. 3,864,124 and 4,153,661. Recently, enthusiasm for immobilizing enzymes has been summarized by T. H. Maugh II in "A Renewed Interest in Immobilized Enzymes", Science, 223, 474-476 (1984).

Immobilization of microorganisms on supports such as agar, alginate, carrageenan, cellulose, polyacrylate, and polyamide has been described by S. Birnbaum, P. Larson, and K. Mosbach in "Solid Phase Biochemistry," W. H. Scouten, Ed., Wiley, 1983, vol. 66, chapter 15. U.S. Pat. No. 4,434,231 describes processes for embedding microorganisms within a matrix of a polymer gel, and U.S. Pat. No. 4,452,892 teaches immobilization of biologically active material in a hydrogel on a support.

U.S. Pat. No. 4,456,685 discloses polyurethane foams to which are bound aspartase-producing microorganisms.

Confining microbials to one side of a membrane filter in a dialyzer has been reported by W-W Tso and W-P Fung, Biotechnol. Lett., 3, 421 (1981) and microbial cells immobilized in a collagen membrane, which was placed over the Teflon ® membrane of an oxygen electrode, was described by R. K. Kobos, Trends in Analytical Chemistry, 2, 143 (1983).

SUMMARY OF THE INVENTION

Briefly, the present invention provides articles which can be in the form of microporous films, composite sheets, fibers, granules and the like comprising a fibrillated polytetrafluoroethylene (PTFE) matrix containing enmeshed and immobilized therein viable cells capable of their usual and continuous biochemical and biological performances. For example, yeast can convert sugar solution to alcohol and Bacillus can convert sugar solution to carboxylic acids.

In another aspect, the present invention provides a method for the preparation of the above-described articles comprising trapping, enmeshing, and immobilizing viable cells within a fibrillated PTFE matrix.

In the present invention viable cells are immobilized by entrapment in a fibrillated polytetrafluoroethylene network which constitutes a composite sheet. Despite the work-intensive nature of the method and the extraordinarily high localized pressure during processing, the resultant viable cells, generally isolated individually and restrained on all sides by a cage of fibrillated PTFE, surprisingly and unexpectedly, remain viable. In such microporous constructions, each immobilized viable cell can be in intimate contact with moving nutrient solution (this is in contrast to gelled polymers as in prior art constructions, through which nutrient must diffuse only very slowly.) Consequently, local concentration of viable cell products are kept low and the viable cells continues to thrive as if in a medium in which the cells' waste products are removed continuously. The system acts like a reactive zone in which the viable cells are captive and the organism waste products (which may be useful products of commerce) are continuously removed. In another embodiment, the nutrients for the viable cells may be toxic or environmentally undesirable and are converted to an environmentally acceptable product(s) by the organism.

In the present application:

"matrix" means an open-structured entangled mass of microfibers;

"viable cell" means any living organism (biological cell or cells) having a diameter of at least 0.1 micrometer including animal, bacterial, fungal, and yeast forms;

"biochemical performance" means capability of converting a compound into another compound of different chemical composition by a biochemical reaction;

"biological performance" means the ability to provide a chemical transformation by a biochemical reaction.

DETAILED DESCRIPTION

Figure 1:
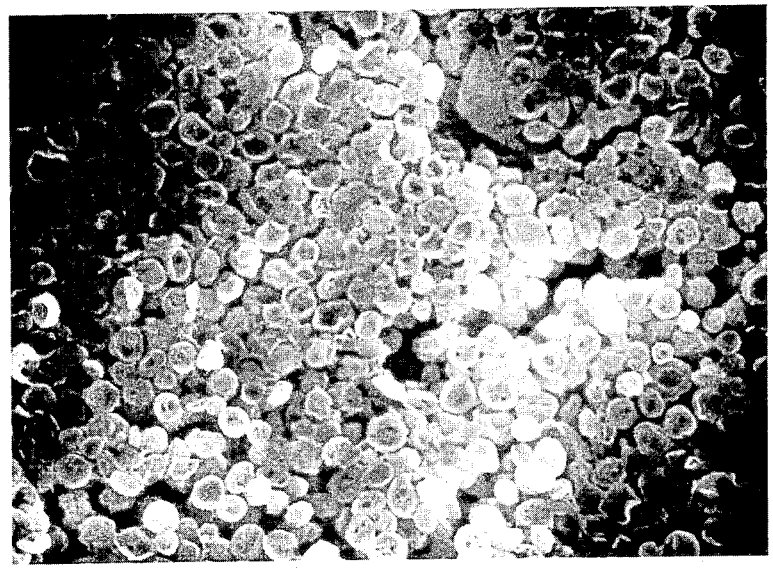
FIG. 1 is a cross-sectional view of a scanning electron microscope photograph (SEM) (enlarged 1000 ×) of a yeast cake which has been frozen and fractured.
Figure 2:
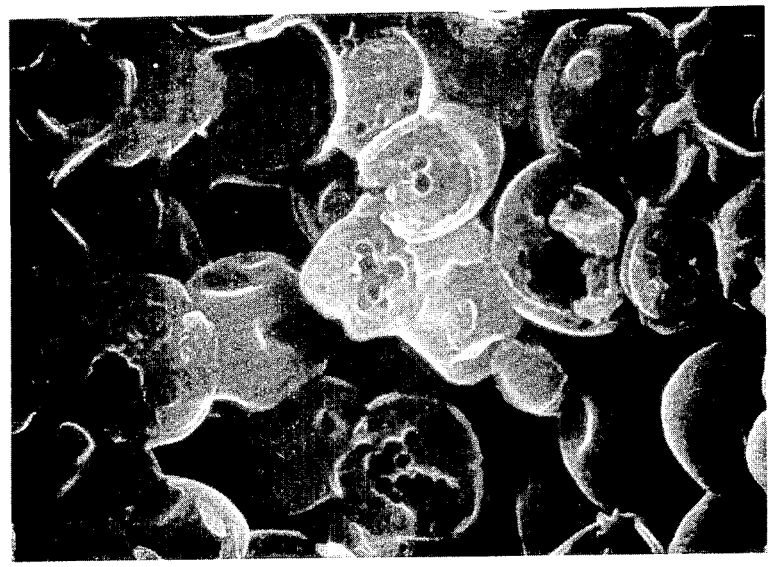
FIG. 2 is a view the SEM of FIG. 1 enlarged fivefold for a magnification of 5000 ×.

The present invention provides a composite structure comprising
(a) a polytetrafluoroethylene fibril matrix, and
(b) 0.005 to 15 parts of viable cells, preferably microorganisms, per part of PTFE by weight immobilized in the matrix, the viable cells being capable of their usual and continuous biochemical and biological performances.

The present invention teaches the immobilization of viable cells, which preferably are microorganisms, in fibrillated polytetrafluoroethylene composite sheets and articles made therefrom.

Viable cells, particularly microorganisms, that are of special interest in this invention are unicellular organisms although multicellular organisms are also included. These organisms are by nature complex cells capable of conducting all the biochemical reactions necessary to their existance, nutrition, and reproduction.

Examples of microorganisms that are useful in the present invention are *Achromobacter guttatus, Azotobacter aqilis, Candida tropicalis, Clostridium butyricum, Escherichia coli, Micrococcus denitrificans, Pseudomonas mephitica* var. *lipolytica, Saccharomyces cerevisiae, Streptococcus faecalis,* and *Tetrahymena pyriformis*. Examples of mammalian cells include bovine cells. Fungal cells include *Aspergillus niger*.

Examples of microorganisms which are especially useful in this invention are *Saccharomyces cerevisiae* and *Bacillus thuringiensis*. Also useful are mammalian cells such as those used in tissue culture.

The size of the viable cells can be within a broad range of 0.1 to 25 micrometers in diameter when dry. Preferably, the particle diameter size range of the viable cells is 0.1 to 15 micrometers. The viable cells are capable of surviving calendering procedures involving localized pressures in the range of 1000 mega pascals (MPa) to 3000 MPa and heat in the range of 30° to 45° C. The viable cells can have a sorptive capacity in the range of 2 to 20 grams of water per gram of dry cells.

It is surprising that viable cells can survive the rigorous conditions necessary to prepare the fibrillated PTFE fibril matrix of the present invention. The PTFE composites can vary in thickness in the range of 0.2 mm to 10 mm. The composites are usually in the form of a sheet, which is very conformable and can be fashioned into any shape [e.g., bent (i.e., even wound around a rod 4 mm in diameter), corrugated, tubular, etc.]. Various shapes can be prepared by extruding, wrapping, or bending the calendered PTFE sheets with particulate therein.

Bioactive materials of the present invention can be prepared from microbiological cells and PTFE emulsion via a variation of the work intensive procedure described in U.S. Pat. No. 4,153,661, which procedure is incorporated herein by reference.

Similar to the method of U.S. Pat. No. 4,153,661, which discloses a polytetrafluoroethylene composite sheet containing nonliving particulate the viable cells useful in the instant invention can be pre-mixed with a diluent which can function, for example, as support, host, nutrient, or processing aid. Representative diluents can be calcium carbonate, kaolin, starch, sugar, polyethylene, zeolites, chitin, Sephadex ®, cellulosics, vermiculite, clay, and the like. These diluent materials can be present in an amount in the range of 0 to 14.995 parts per part of PTFE, provided that the viable cells plus diluent do not exceed 15 parts particulate to 1 part PTFE. These ranges are desirable to achieve a preferred tensile strength of at least 1.7 MPa in the composite structure.

The present invention provides a novel composite structure and method therefore, the composite structure preferably being a uniformly porous, high void-volume composite sheet comprised of viable cells distributed uniformly throughout a matrix formed of interentangled, fibrillated PTFE fibrils. In such a structure almost all of the cells are separate one from another and each is isolated in a cage that restrains the cell on all sides by a fibrillated mesh of PTFE microfibers. The preferred novel sheet of the invention has a high tensile strength of at least 1.7 MPa (250 PSI), and even as high as 13.6 MPa (2000 PSI), and is substantially uniformly porous, making it suited for use as a filtering material for pollution control, for preparation of specific chemicals, for example, antibiotics, and generation of usual fermentation products such as ethanol, acetone, and butyl alcohol, and even hormones, and for many other purposes which can be envisioned in the art for such materials. The method requires neither organic lubricants nor extraction of a removable additive material to produce porosity.

The method involves first blending the viable cells with a PTFE aqueous dispersion into a damp paste and then adding sufficient lubricant water to exceed the absorptive capacity of the solids in the mixture yet maintain a putty-like consistency. The resultant putty-like mass is then intensively mixed at a temperature between 5° and 70° C., preferably between 20° and 40° C. to fibrillate initially the PTFE particles and, while maintaining the same water content, the resultant mass is biaxially calendered between heated calendering rolls maintained at about 5° to 70° C., preferably 30° to about 40° C. to cause further fibrillation, producing a composite sheet which, optionally, is then dried. The exact temperatures used are dictated by the sensitivity of the cells. The desired thickness of the film (0.2 to 10 mm) is determined by the final spacing of the rollers.

Biaxial calendering is accomplished by rotating a calendered sheet at 90° to the calendering machine direction and repeating the calendering operation with a reduction of the space between the calendering rolls or including folding the calendered sheet on itself before rotating or both. Such calendering provides uniform multidirectional fibril formation, imparting a high degree of tensile strength in the resultant sheet.

The dried resultant composite comprises viable cells and PTFE fibrils in a weight ratio of about 0.005:1 to 15:1 viable cells material to PTFE fibrils. For the most part, the PTFE fibrils will have a diameter in the range of about 250Å to 250Å. The composite is preferably characterized by having a tensile strength of at least 1.7 MPa. Depending on the nature of the viable cells in the construction, the article can be stored dried or hydrated.

These are several key steps which are required in the method of the invention to produce the unique high tensile strength PTFE composite of the invention. The initial intensive mixing is accomplished at a temperature between about 5° and 70° C., preferably at an elevated temperature between 20° and about 40° C. or the sheet will not have a sufficiently high tensile strength. Additionally, the water content of the putty-like mass being processed should be maintained above or near the absorptive capacity of the solids therein or else proper fibrillation will not occur.

The viability of films of the invention made from dried yeast has been demonstrated. It has been shown qualitatively that when these composite membranes are placed in conventional glucose nutrient solutions, conversion to ethanol begins soon thereafter, i.e. after three hours the aqueous solution contained 0.15% ethanol (as determined by chromatographic analysis).

Viable cells in the PTFE microfiber mesh can be in their natural environment, i.e., in the aqueous media on which they feed. This combination of physical integrity and natural efficacy permits maximal versatility in design of apparatus for applications.

Before preparing the composite sheet of the invention it may be desirable to remove certain additives in commercially available PTFE. For example, Teflon ® emulsion 30-B (Dupont) contains about 60 weight percent PTFE and 8 weight percent surfactant. To minimize any possible undesirable or toxic effect of such surfactant or other additives already present in commercially available emulsions, the PTFE enmeshed product is washed thoroughly to remove such materials (see Example 1, below).

Composite films of the invention are excellent surface filters for viable cells as small as E. coli and even pseudomonads. It is anticipated that this technology may be a general method for immobilization of all viable cells perhaps with cell diameters of at least 0.1 micrometer.

The articles of this invention are useful as industrial catalysts in continuous and batch operations in such processes as organic synthesis, fermentation, removal of chemical pollutants and the like, manufacture of many items of commerce such as ethanol, carboxylic acids, antibiotics, hormones and other biochemicals.

It is also anticipated that the composite structures of the present invention will have applications such as photobiogeneration of $H_2$ and $O_2$ from $H_2O$: collection of heavy metals from aqueous solution; selective oxidation of organic feedstocks, and generation of the usual fermentation products such as acetone, ethanol, or butyl alcohol.

Objects and advantages of this invention are further illustrated by the following examples, but the particular materials and amounts thereof recited in these examples, as well as other conditions and details, should not be construed to unduly limit this invention.

In the following EXAMPLES, all temperatures are stated in degrees Centigrade.

EXAMPLE 1

Preparation and Use of a Microporous Composite membrane in the form of a film consisting of *Sacchromyces cerevisiae* (85%) enmeshed in polytetrafluoroethylene microfibers (15%).

To 25 g of powdered *Saccharomyces cerevisiae* (dried Fleischmann's yeast, Nabisco Brands, Inc., East Hanover, N.J.) was added 15 ml of distilled water to produce a smooth paste. An aqueous emulsion (16 ml) of polytetrafluoroethylene (PTFE, E. I. duPont de Nemours, Wilmington, Del. under the designation Teflon TM 30-B, having a 59.7% solids content and reduced in this example by dilution with water to 22.5% solids) was added dropwise to this paste, which was kneaded continuously in a mortar and pestle to produce a stiff dough. It was worked on a rubber mill kept at 40° C. essentially as described in U.S. Pat. No. 4,373,519 to produce a tough film or sheet with a slippery intestine-like texture. Attempts to air-dry the film or sheet in the usual way lead to a rigid film that fractured on folding, owing to agglutination of the particles, probably by hydrogen bonding. Reimmersion of the film in water led to regeneration of the flexible intestine-like texture. Drying the film under tension, however, produced a soft, microporous (greater than 50% voids), pliable, drapable film that could be wound around a 6.3 mm (¼ inch) rod without damage to the film.

Since the original commercially available polytetrafluoroethylene emulsion and the resultant film made therefrom contained about 8% polyalkyleneoxide hydrocarbon soap for stabilization, this soap was removed by immersion of the composite film in a water bath through which warm (less than 40° C.) water was circulated slowly for about 18 hours. Samples of the soap-free film (0.025 cm thick; water swollen or air-dried under tension) were cut in the form of circles 44.2 square cm in area and then positioned on the macroporous plate of an Amicon (Danvers, Mass.) 402 Model 3155 ultrafiltration cell. Tap water (1.2 L) that was previously sterilized by boiling was made to permeate the reactive membrane film under 0.68 atmospheres of hydrodynamic pressure.

The rate of flow, F (ml/min) through the membrane film decreased with the total volume V (L) of water permeating the film as given by the expression:

$$\log F = 1.52 - 0.280 \, V$$

which implies that the permeability was decreasing in the usual way owing to adsorption of hydrophobic impurities on the low pressure side of the macroporous membrane film (see L. A. Errede and P. D. Martinucci, Ind. Eng. Chem. Res. & Dev., 19, 573 (1980)). When the water was replaced by a standard nutrient solution, the flow rate decreased from 18 ml/min at $v = 1.2$ L to 1.5 ml/min at $v = 1.3$ L, and decreased logarithmically thereafter according to the expression $$\log F = 0.176 - 0.213 \, (V - 1.2)$$

even when the nutrient solution was replaced in turn by sterilized tap water. This sharp decrease in flow rate was caused by accumulation of solvated protein molecules, now in the form of a gel, which were removed by filtration at the high pressure side of the membrane filter. When this gel was removed by physical delamination at v=2.0 L, the water permeability was restored to that exhibited at v=1.2 L, that is, F=19 ml/min at 0.68 atmospheres.

The membrane film was then permeated by 1.4 L of freshly distilled water, during which time the flow rate at 0.68 atmosphere remained constant, F=19 ml/min. The distilled water was then replaced by 1% glucose (0.06 M) in distilled water and the flow rate F=13.8 ml/min at 0.68 atmosphere remained constant.

The percent alcohol generated (see TABLE I below) during passage of the glucose solution through the reactive membrane film containing the trapped yeast cells was determined by gas chromatography of the filtrate and was found to be independent of the total volume of 1% glucose solution but very dependent upon residence time, t, in the reaction zone, where t=volume of membrane/flow rate of permeate, or
t=44.2×0.025 cc/F(cc/min), or
t=1.1/F min as shown by the following data:

TABLE I

| Sample | Pressure (mm Hg) | Flow Rate (F) (ml/min) | Residence Time (t) (min) | Ethanol (ppm) | % theory |
|---|---|---|---|---|---|
| Control | — | — | 0 | 0 | 0 |
| 1 | 513 | 19 | 0.06 | 1 | 0.03 |
| 2 | 41 | 1.5 | 0.7 | 10 | 0.3 |
| 3 | 1.1 | 0.04 | 28 | 440 | 15 |
| 4 | 0.8 | 0.63 | 37 | 690 | 23 |
| 5 | 0.5 | 0.02 | 55 | 910 | 30 |

The date of TABLE I show that the percent conversion of reactant to product is a linear function of the residence time (t).

Figure 3:
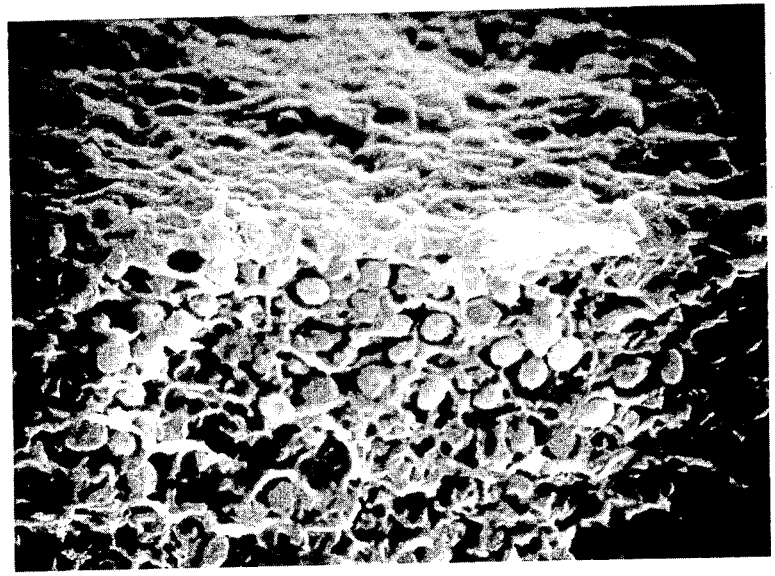
FIG. 3 is a SEM photograph (enlarged 1000 ×) of the surface and fractured edge of a composite microporous membrane film having yeast (85 weight percent) immobilized in PTFE microfibers (15 weight percent), viewed tilted down 15 degrees from the horizontal.
Figure 4:
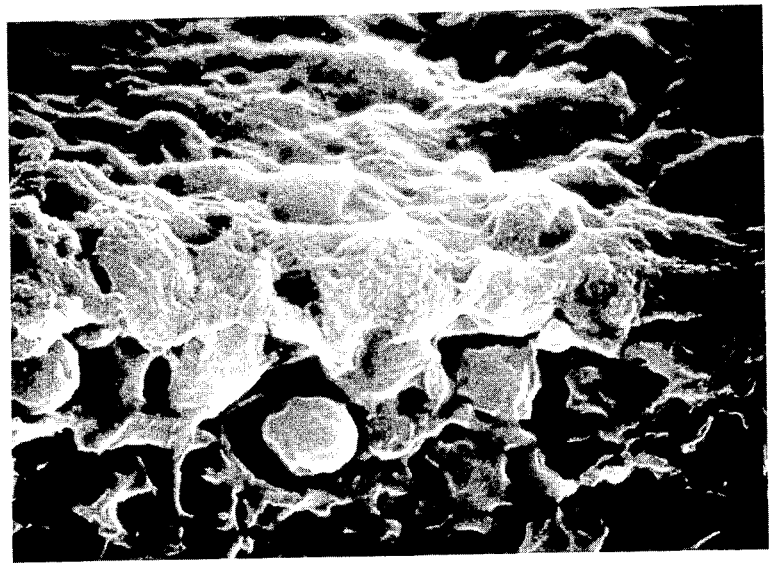
FIG. 4 is a view of the SEM of FIG. 3 enlarged three-fold for a magnification of 3000 ×.
Figure 5:
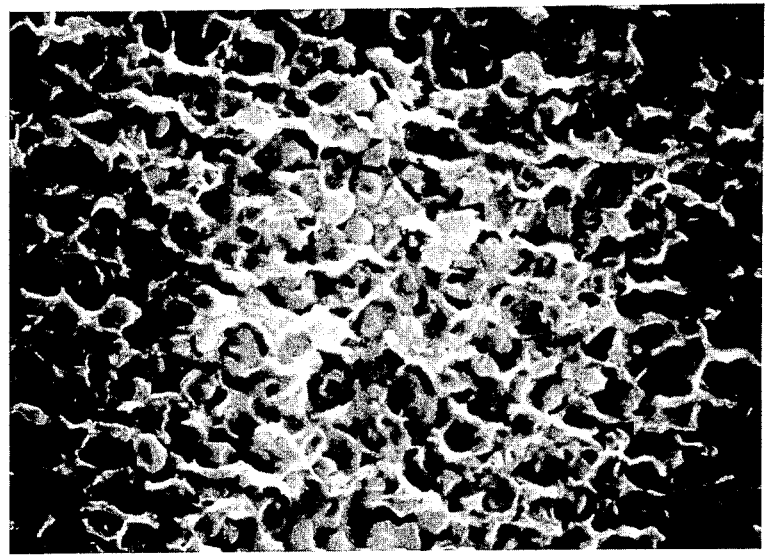
FIGS. 5 and 6 are SEM microphotographs (enlarged 1000 × and 5000 ×, respectively) of the freeze-fractured edge (of yeast immobilized in a PTFE fibril matrix) at a zero degree orientation (horizontal view).
Figure 6:
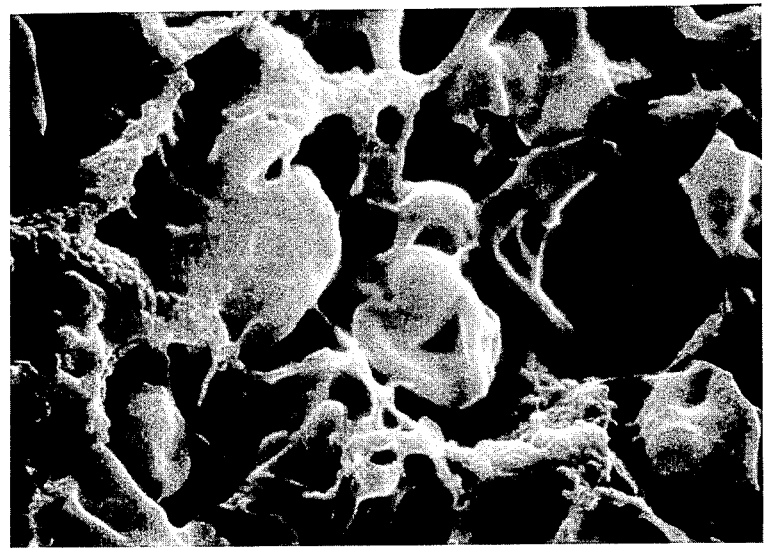

FIGS. 3 to 6 of the Drawing show that almost all microbiological cells (85%) are isolated individually and immobilized in individual "compartments" by PTFE microfibers (15%). It can be seen that the yeast cells are isolated in the microporous PTFE fiber enclosures. The cells are uniformly distributed both vertically and horizontally in linear planes that parallel the surface of the composite film. When wet, the cells are fully swollen and the physical appearance and texture of the film is that of a rubber-like sheet; but when dried under tension, the film texture and appearance is that of kid-leather.

EXAMPLE 2

Viability of Yeast Cells Enmeshed in the PTFE Composite Membrane Film

A thin strip was cut from a PTFE microporous membrane as used in EXAMPLE 1 and inserted in a standard nutrient solution kept at 27° C. such that the cells at the cut edge of the strip were free to escape from the membrane. These cells multiplied rapidly and generated copious quantities of carbon dioxide indicating continued cell viability. The yeast cells remained viable even after the composite film was used for one week as a reactive membrane.

EXAMPLE 3

Preparation and Use of a Microporous Composite membrane film consisting of *Bacillus thuringiencis* (85%) enmeshed in polytetrafluoroethylene microfibers (15%).

To 8 g of powdered *Bacillus thuringiencis* (Dipel hg TM, Burgess vibrocrafters, Ind., Grayslake, Ill.) was added 12 ml of distilled water to produce a smooth paste to which was then added dropwise 10 ml of aqueous PTFE emulsion (24% solids) while the mixture was being kneaded in a mortar and pestle to provide a tough dough. It was worked on a rubber mill kept at about 40° C. in the usual way to produce a tough amber rubber-like film that was 0.025 cm thick. This film was washed overnight in warm water to remove soaps and impurities as described in EXAMPLE 1. The amber color and the strong odor associated with these samples were removed completely during this washing step to produce an odorless and colorless (i.e., white) membrane film. Circular samples (44.2 square cm) were cut from this film (0.025 cm thick) for use as the reactive membrane film positioned at the bottom of an Amicon 402 Model 3155 ultrafiltration cell. The film was then permeated sequentially by 0.4 L of sterilized tap water, standard nutrient solution, and distilled water. The flow patterns exhibited during these sequential changes in aqueous permeate were essentially the same as those described in EXAMPLE 1. Finally, the membrane film was permeated by 1% glucose in distilled water and the amount of carboxylic acid generated and collected in the permeate was determined by gas chromatography. As in EXAMPLE 1, the percent conversion to acid products was independent of the volume (v) of liquid that permeated the membrane, but strongly dependent upon the residence time (t) in the reaction zone as shown by the data of TABLE II:

TABLE II

| Sample | Pressure (atm) | Flow (ml/min) | Time (t) (min) | Carboxylic Acid (ppm) | U[a] (ppm) | % theory[b] |
|---|---|---|---|---|---|---|
| control | — | — | 0 | 0 | 0 | 0 |
| 1 (V = 1.4)[c] | 2 | 13 | 0.1 | 2 | 1 | 0.1 |
| 2 (V = 1.8) | 2 | 13 | 0.1 | 2 | 1 | 0.1 |
| 3 (V = 3.0) | 2 | 13 | 0.1 | 2 | 1 | 0.1 |
| 4 (V = 4.4) | 0.0015 | 0.01 | 110 | 2000 | 500 | 83 |

[a]U is an unidentified compound
[b]based on two carbon-containing molecule (e.g., acetic acid)
[c]V is cumulative volume of glucose solution in liters that permeated the membrane The data of TABLE II show that the percent conversion of reactant to product is a function of residence time.

Again, photographs of SEM images of freeze-fractured samples after use in the example above showed that the microorganisms were isolated and trapped in the open, micropore structure of the PTFE membrane film.

EXAMPLE 4

Strips cut from the PTFE miroporous membranes used in EXAMPLE 3 were immersed in a nutrient solution and the viable cells at the cut edge of the strip, which were free to escape from the membrane, multiplied rapidly indicating the viability of the microorganisms even after fabrication and a week of use as a reactive membrane film.

EXAMPLE 5

Preparation and Use of a Microfibrous Network of Pseudomonas Entrapped in PTFE.

A wet mass (18.7 g) of *Pseudomonas aeruginosa* (0.203 g dry Pseudomonas per gram of wet mass) was mixed with 16 g of Sephadex ® (Pharmacia Fine Chemicals Co., Sweden) that contained 50% water. To this mixture was added dropwise with constant stirring 8 g of Teflon ® 30-B aqueous emulsion, which contained 60 weight percent PTFE and 8 weight percent non-ionic soap. The mixture was converted to a tough membrane at room temperature by a work intensive procedure using an ordinary rubber mill as described previously. The membrane obtained thereby was tumbled in a water bath for 24 hours to remove the soap solution. A circular sample (44.2 cm$^2$ × 0.2 cm thick = 8.82 cm$^3$) was cut from the water swollen membrane. Another sample was used to determine that the water swollen sample contained 2.1 g water per gram of dry composite, i.e., the weight of Pseudomonas in the 8.8 cm$^3$ of membrane was 8.8 × 1/3.1 × 3.8/(3.8g Pseudomonas + 8g Sephadex + 5g PTFE) = 0.64g. The 8.8 cm$^3$ membrane was fitted to a Amicon TM ultrafiltration cell with 430 ml capacity. Four hundred and twenty ml of distilled water was forced at 0.3 MPa (45 PSIG) through the membrane. The rate of flow at this pressure was 2.5 cm$^3$/hr. Hence, the residence time was 3.5 hours.

An additional 420 ml of distilled water was allowed to permeate through the membrane over a period of 28 days via gravity feed. A 1% solution by weight of trypticase soy-broth was allowed to permeate the membrane for three additional days followed by 420 ml of distilled water. The reservoir was then charged with an aqueous solution of 2,4,5-trichlorophenoxyacetic acid (21 parts per million) which was forced at 0.28 MPa (41 PSIG) through the membrane (8.8 cm$^3$) at the rate of 8 ml/hr. Thus, the residence time in the membrane was 1.1 hours. The amount of 2,4,5-trichlorophenoxyacetic acid (2, 4, 5-T) in the eluate was determined by gas chromatography. The percent efficiency of removal at this residence time is given in TABLE III below as a function of days in operation.

TABLE III

| | | | | | |
|---|---|---|---|---|---|
| Time in days that membrane was in use | 32 | 33 | 34 | 35 | 36 |
| Time in days exposed to 2,4,5-T | 1 | 2 | 3 | 4 | 5 |
| Percent removal | 23 | 17 | 16 | 8 | 0 |

This data show that even Pseudomonas cells which were not conditioned to tolerate 2,4,5-T, after exposure to the membrane can be utilized to remove the toxicant 2,4,5-T for a period of at least 4 days. Additional trials showed that 2,4,5-trichlorophenoxyacetic acid was not removed when Sephadex alone was used as the only component other than PTFE in a composite membrane.

Various modifications and alterations of this invention will become apparent to those skilled in the art without departing from the scope and spirit of this invention, and it should be understood that this invention is not to be unduly limited to the illustrative embodiments set forth herein.

We claim:

1. A method of preparing a compsite structure consisting essentially of a polytetrafluoroethylene fibril matrix having entrapped therein 0.005 to 15 parts of viable cells per part of polytetrafluoroethylene by weight, said viable cells being capable of their usual and continuous biochemical and biological performances comprising the steps of:
   (a) providing a blend consisting essentially of viable cells and surfactant-and soap free polytetrafluoroethylene as an aqueous dispersion in the form of a damp paste,
   (b) adding sufficient water as a lubricant to exceed the absorptive capacity of the viable cells yet maintain a stiff dough consistency
   (c) intensively mixing said stiff dough at a temperature in the range of 5° to 70°C. to fibrillate said polytetrafluoroethylene, and
   (d) biaxially calendering the resultant mass between calendering rolls at a temperature in the range of 5° to 70° C. and a pressure in the range of 1000 to 3000 MPa to cause further fibrillation of said polytetrafluorethylene to provide said composite structure, said heating being controlled to preserve the viability of the cells.

2. The method according to claim 1 wherein said viable cells range in size from 0.1 to 25 micrometers.

3. The method according to claim 1 wherein said viable cells range in size from 0.3 to 15 micrometers.

4. The method according to claim 1 wherein said calendering rolls are maintained at a temperature in the range of 30° to 40° C.

5. The method according to claim 1 wherein said mixing in (c) takes place at a temperature in the range of 20° to 40° C.

6. The method according to claim 1 wherein said viable cells are *Achrombacter guttatus, Azotobacter aqilis, Candida tropicalis, Clostridium butyricum, Eschericia coli, Micrococcus denitrificans, Pseudomonas mephitica* var. *lipolytica, Saccharomyces cerevisiae, Streptococcus faecalis, Tetrahymena pyriformis, Aspergillus niger, Bacillus thuringiensis* or mammalian cells.

7. The method according to claim 1 wherein said composite structure further consists essentially of a cell nutrient which is added in step (a).

8. The method according to claim 1 wherein said composite structure further consists essentially of at least one processing aid selected from the group consisting of calcium carbonate, starch, polyethylene, zeolite, chiten, Sephadex, cellulosics, vermiculite and clay which is added in step (a).

9. The method according to claim 1 further comprising the step of drying the resultant composite structure from step (d).

10. A composite structure consisting essentially of a polytetrafluoroethylene fibril matrix having entrapped therein 0.005 to 15 parts of viable cells per part of polytetrafluoroethylene by weight, said viable cells being capable of their usual and continuous biochemical and biological performances, said composite having been prepared by a process comprising the steps of:
   (a) providing a blend consisting essentially of viable cells and surfactant-and soap-free polytetrafluoroethylene as an aqueous dispersion in the form of a damp paste.
   (b) adding sufficient water as a lubricant to exceed the absorptive capacity of the viable cells yet maintain a stiff dough consistency,
   (c) intensively mixing said stiff dough at a temperature in the range of 5° to 70° C. to fibrillate said polytetrafluoroethylene, and (d) biaxially calendering the resultant mass between calendering rolls at a temperature in the range of 5° to 70° C. and a pressure in the range of 1000 to 3000 MPa to cause further fibrillation of said polytetrafluoroethylene to provide said composite structure, said heating being controlled to preserve the viability of the cells.

11. The composite structure according to claim 10 further consisting essentially of a cell nutrient which has been added in step (a).

12. The composite structure according to claim 10 further consisting essentially of at least one processing aid selected from the group consisting of calcium carbonate, starch, polyethylene, zeolite, chiten, Sephadex, cellulosics, vermiculite and clay which has been added in step (a).

13. The composite structure according to claim 10 further comprising the step of drying the resultant composite structure from step (d).

* * * * *

UNITED STATES PATENT AND TRADEMARK OFFICE
CERTIFICATE OF CORRECTION

PATENT NO. : 4,722,898

DATED : February 2, 1988

INVENTOR(S) : Errede et al.

It is certified that error appears in the above-identified patent and that said Letters Patent is hereby corrected as shown below:

Col. 5, line 7, after "to", "250 Å" should read --2500 Å--.

Col. 5, line 59, "$H_2O$:" should read --$H_2O$;--.

Col. 9, line 66, "compsite" should read --composite--.

Signed and Sealed this

Ninth Day of July, 1991

Attest:

HARRY F. MANBECK, JR.

Attesting Officer

Commissioner of Patents and Trademarks